(12) United States Patent
Von Dach et al.

(10) Patent No.: US 7,574,917 B2
(45) Date of Patent: Aug. 18, 2009

(54) METHOD FOR IN-SITU MEASURING OF ACOUSTIC ATTENUATION AND SYSTEM THEREFOR

(75) Inventors: Thomas Von Dach, Cressier (CH); Samuel Harsch, Ballaigues (CH)

(73) Assignee: Phonak AG, Staefa (CH)

( * ) Notice: Subject to any disclaimer, the term of this patent is extended or adjusted under 35 U.S.C. 154(b) by 405 days.

(21) Appl. No.: 11/457,185

(22) Filed: Jul. 13, 2006

(65) Prior Publication Data

US 2008/0011084 A1    Jan. 17, 2008

(51) Int. Cl.
*G01H 17/00* (2006.01)
*H01R 29/00* (2006.01)

(52) U.S. Cl. .......................... 73/646; 181/135; 381/60; 381/58

(58) Field of Classification Search .................. 73/584, 73/646; 324/602; 381/58–60
See application file for complete search history.

(56) References Cited

U.S. PATENT DOCUMENTS

| | | | |
|---|---|---|---|
| 3,729,598 A * | 4/1973 | Tegt et al. ...................... | 381/58 |
| 3,968,334 A | 7/1976 | Padilla | |
| 4,060,701 A | 11/1977 | Epley | |
| 5,577,511 A | 11/1996 | Killion | |
| 6,533,062 B1 | 3/2003 | Widmer et al. | |
| 6,567,524 B1 | 5/2003 | Svean et al. | |
| 6,687,377 B2 * | 2/2004 | Voix et al. ..................... | 381/60 |
| 6,766,878 B2 | 7/2004 | Widmer et al. | |
| 2004/0086138 A1 | 5/2004 | Kuth | |
| 2005/0123146 A1 | 6/2005 | Voix et al. | |
| 2006/0137934 A1 * | 6/2006 | Kurth ......................... | 181/135 |
| 2007/0147635 A1 * | 6/2007 | Dijkstra et al. ............. | 381/94.1 |

FOREIGN PATENT DOCUMENTS

| | | |
|---|---|---|
| DE | 10117705 A1 | 10/2001 |
| EP | 1674059 A1 | 6/2006 |
| GB | 2261950 A | 6/1993 |
| WO | 2005/055656 A1 | 6/2005 |

* cited by examiner

*Primary Examiner*—Hezron Williams
*Assistant Examiner*—Nashmiya S Fayyaz
(74) *Attorney, Agent, or Firm*—David S. Safran; Roberts Mlotkowski Safran & Cole, P.C.

(57) ABSTRACT

There is provided a method for measuring in-situ the acoustic attenuation obtained by a hearing protection device worn by a user, comprising: positioning the hearing protection device comprising a microphone oriented towards the user's ear canal at the user's ear;
positioning a cup-like measuring device comprising a loudspeaker oriented towards to user's ear and a microphone oriented towards to user's ear at the user's ear in such a manner that a closed space surrounding the hearing protection device is created by the measuring device;
providing a test signal via the loudspeaker, capturing audio signals representative of the level of the test signal in the closed space by the microphone of the measuring device and capturing audio signals representative of the level of the test signal in the user's ear canal by the microphone of the hearing protection device; processing the audio signals captured by the microphone of the measuring device and the audio signals captured by the microphone of the hearing protection device and estimating the attenuation provided by the hearing protection device from the processed audio signals.

21 Claims, 4 Drawing Sheets

METHOD FOR IN-SITU MEASURING OF ACOUSTIC ATTENUATION AND SYSTEM THEREFOR

BACKGROUND OF THE INVENTION

1. Field of the Invention

The present invention relates to a method and a system for measuring in-situ the acoustic attenuation provided by a hearing protection device worn by a user.

2. Description of Related Art

U.S. Pat. No. 6,687,377 B2 relates to a method for measuring the acoustic attenuation provided by a customized earplug, wherein the earplug is provided with a sound bore extending from the outer side of the earplug to the inner end of the earplug, wherein a remote device is inserted into the outer end of the sound bore, which remote device comprises a first microphone oriented towards the sound bore and a second microphone oriented towards ambience, and wherein test sound is provided by an external loudspeaker. Both the loudspeaker and the remote device are connected to a computer unit on which a measurement program is run. The acoustic attenuation provided by the earplug is calculated from the sound level difference between the first microphone and the second microphone.

U.S. Pat. No. 5,577,511 relates to a method for measuring in-situ the acoustic attenuation provided by an earplug, wherein a probe tube extends through the earplug into the ear canal and wherein the outer end of the probe tube is connected to a first microphone, while a second microphone is provided at the ear for measuring sound pressure levels exterior to the ear canal as a reference microphone. The acoustic attenuation provided by the earplug is calculated from the difference of the sound levels measured by the first and the second microphone. The test sound for the measurement is the user's voice.

U.S. Pat. No. 6,567,524 B1 relates to a customized earplug which comprises an inner microphone oriented towards the ear canal, an outer microphone oriented towards ambience and a loudspeaker oriented towards the ear canal. The earplug may be used for online control and verification of the acoustic attenuation provided by the earplug by generating a test sound by the loudspeaker and analyzing the signal picked up by the inner microphone.

DE 101 17 705 A1 relates to a hearing protection headphone which comprises a microphone oriented towards ambience and into which a hearing protection earplug is integrated which comprises a loudspeaker oriented towards the ear canal and a microphone oriented towards the ear canal for picking up sound in the ear canal for active noise reduction purposes. The microphone of the headphone is used for selectively providing ambient sound to the ear canal via the loudspeaker of the earplug for communication purposes.

It is an object of the invention to provide for a reliable and reproducible method for measuring in-situ the acoustic attenuation provided by a hearing protection device. It is a further object to provide for a corresponding system.

SUMMARY OF THE INVENTION

According to the invention these objects are achieved by a method as defined in claim 1 and a system as defined in claim 15, respectively.

The invention is beneficial in that, by providing the hearing protection device with a microphone oriented towards the ear canal and by using a separate cup-like measuring device which creates a closed space surrounding the hearing protection device and which comprises a loudspeaker for providing a test sound to the closed space and a microphone for picking up the level of the test sound in the closed space, particularly reliable and reproducible in-situ measurements of the acoustic attenuation provided by the hearing protection device can be obtained, since well-defined test conditions are provided by the arrangement of the hearing protection device and the measuring device. In addition, by utilizing this concept, the modifications to the hearing protection device required for the in-situ measurement with regard to a standard hearing protection device can be kept low.

These and further objects, features and advantages of the present invention will become apparent from the following description when taken in connection with the accompanying drawings which, for purposes of illustration only, show several embodiments in accordance with the present invention.

DETAILED DESCRIPTION OF THE INVENTION

Figure 1:
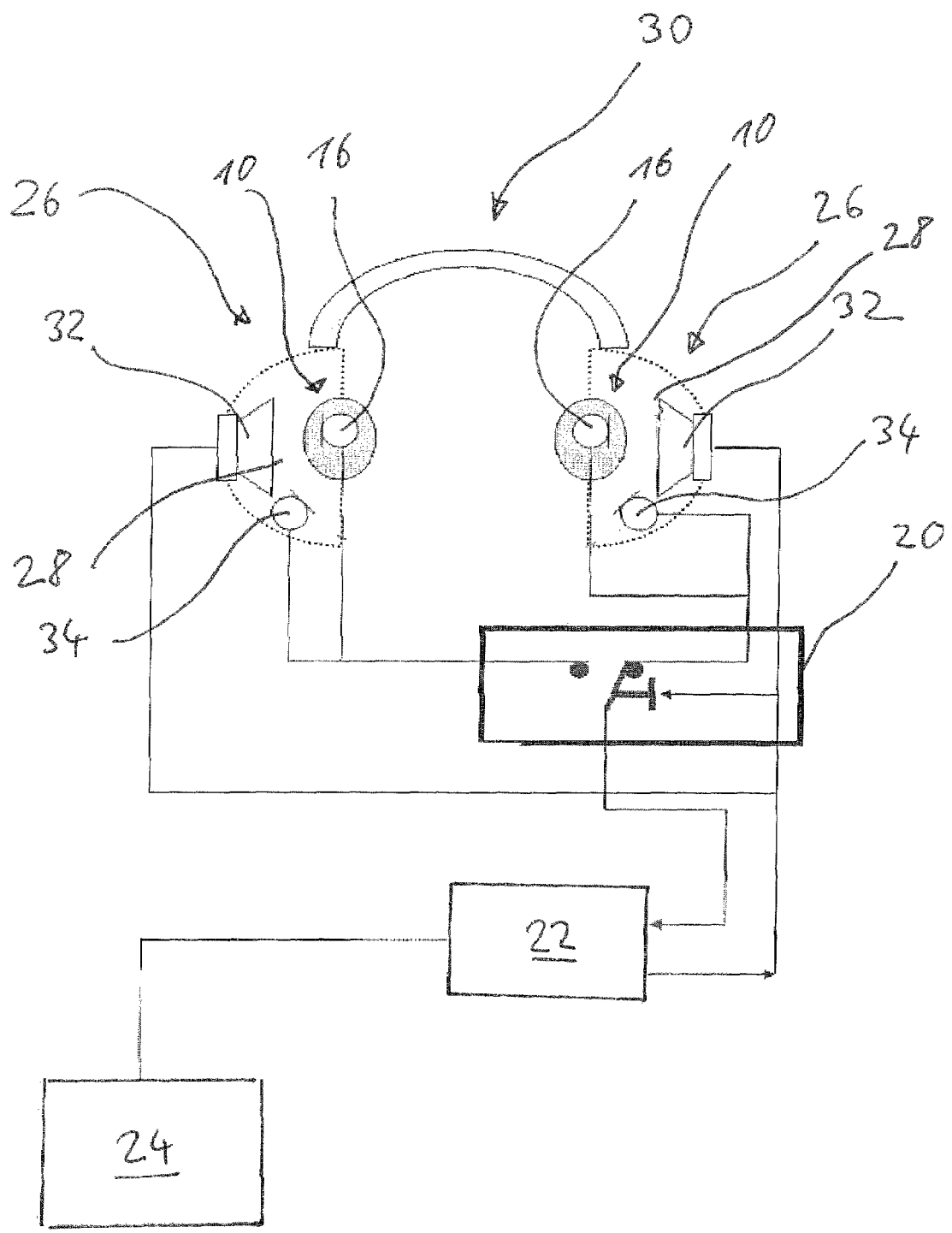
FIG. 1 shows schematically an example of an in-situ acoustic attenuation measurement system according to the invention.

FIG. 1 is a schematic view of a system for measuring the acoustic attenuation obtained by hearing protection device 10 worn by a user. Preferably, the hearing protection device 10 is a customized earplug 10 comprising a hard shell 12 which may have an elasticity from shore D85 to D65 and may be made of polyamide. The earplug 10 is inserted at least in part into the user's ear canal 14 in an attenuation position. In order to achieve optimized fit of the shell 12 within the user's out ear and ear canal, the shell 12 has an outer surface individually shaped according to the measured shape of the user's outer ear and ear canal. The shape of the user's outer ear and ear canal may be determined by direct three-dimensional scanning of the ear canal of the concha or by producing an impression of the ear canal and the concha which subsequently undergoes scanning. The digital data obtained by the scanning process is then used to create the hard shell by an additive or incremental layer-by-layer build-up process. Examples of such processes for producing customized earplugs can be found, for example, in US 2003/0133583 A1 or U.S. Pat. No. 6,533,062 B1.

The earplug 10 includes a microphone 16 which is oriented towards the user's ear canal 14 and the user's ear drum 19 for capturing sound in the ear canal 14. The acoustic connection of the microphone 16 to the ear canal 14 usually will is obtained by providing a corresponding sound passage 18 in the earplug 10, which extends from the microphone 16 to the inner end of the earplug 10.

The microphone 16 is electrically connected to a means for processing the audio signals captured by the microphone 16 from the sound in the ear canal 14. According to the example shown in FIG. 1 the microphone 16 for this purpose may be connected via an automatic switch 20 and a sound card 22 to a computer 24, for example via a USB interface.

Figure 2:
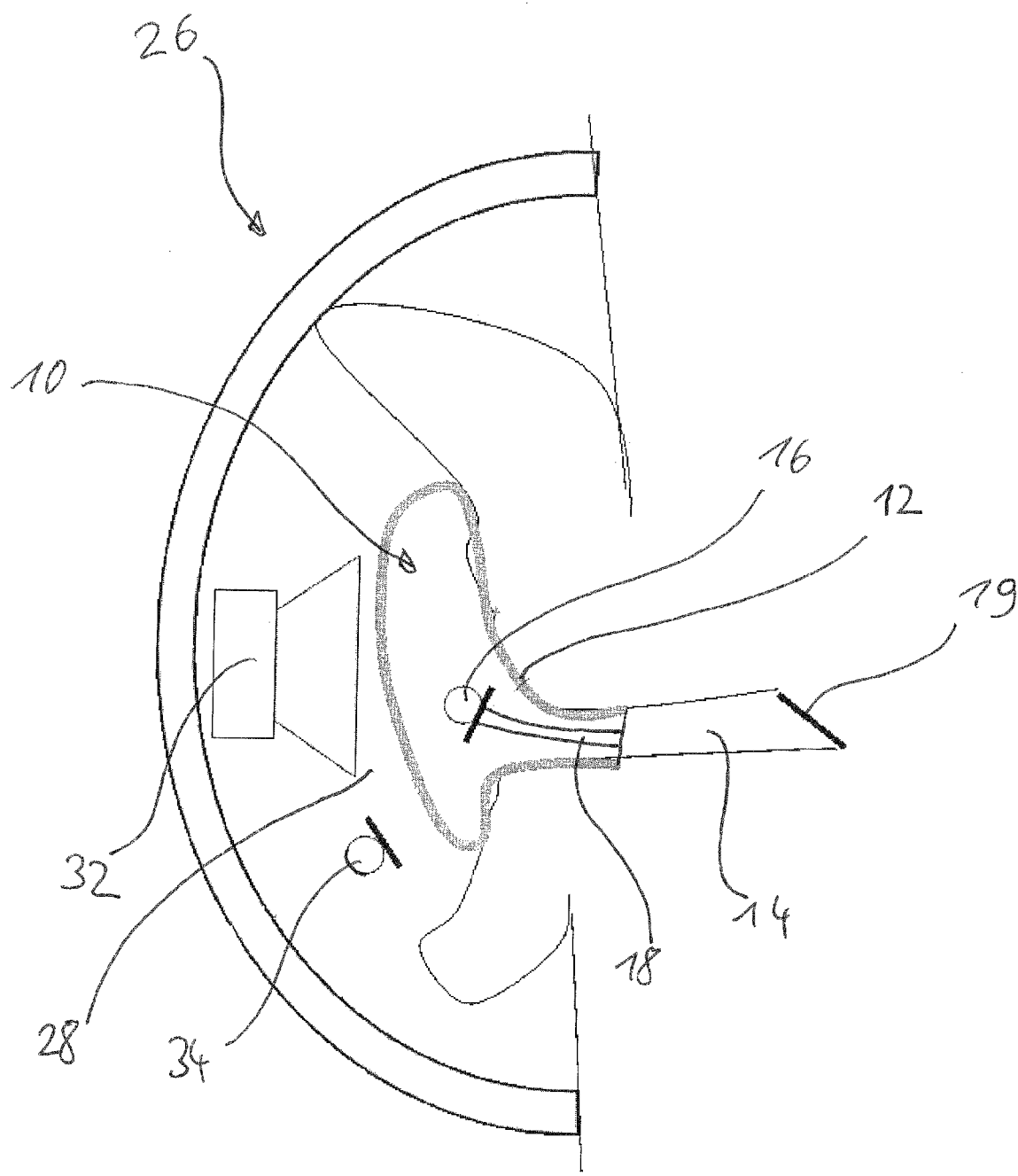
FIG. 2 is a more detailed schematic view of one ear of the user during an in-situ acoustic attenuation measurement.

The system also comprises a cup-like measuring device 26 which is positioned at the user's ear in such a manner that a closed space 28 surrounding the earplug 10 positioned in the ear canal 14 is created by the measuring device 26. Preferably, as shown in FIGS. 1 and 2, the measuring device 26 is one cup of a headphone 30. The measuring device 26 comprises a loudspeaker 32 which is oriented towards the user's ear for providing test sound to the closed space 28 and a microphone 34 which is oriented towards the user's ear for picking up sound in the closed space 28 in order to capture audio signals from the sound in the closed space 28. The microphone 34 is electrically connected via the automatic switch 20 and the sound card 22 to the computer 24, while the loudspeaker 32 is connected via the sound card 22 to the computer 24.

According to FIG. 1, the system is binaural i.e. at each ear an earplug 10 and a measuring device 26 are provided. The switch 20 serves to switch between an acoustic attenuation measurement for the left ear and the right ear, with the measurement being performed subsequently for the two ears.

For carrying-out an in-situ acoustic attenuation measurement first an earplug 10 is inserted into the user's ear canal 14 of his left ear and right ear, respectively. Subsequently, the headphone 30 is positioned at the user's head in such a manner that the closed space 28 is formed within each cup 26 around each earplug 10. The microphones 16, the microphones 34 and the loudspeakers 28 are connected to the computer 24 via the sound card 22. Before the actual measurement starts, an audio signal is generated by the computer 24 and the sound card 22 which sets the switch 20, for example, to the right ear position as shown in FIG. 1. Then a test audio signal is generated by the computer 24 and the sound card 22 and is supplied to the loudspeaker 32 which creates a corresponding test sound in the closed space 28. This test sound is directly picked-up by the microphone 34 of the cup 26, and a corresponding audio signal is supplied via the sound card 22 to the computer 24. Simultaneously the test sound as attenuated by action of the earplug 10 is picked-up by the microphone 16 of the earplug 10 from the ear canal 14 which is acoustically sealed by the earplug 10, and a corresponding audio signal is supplied via the sound card 22 to the computer 24. The audio signals from the microphones 16 and 34 undergo some signal processing, such as recording, Fast Fourier Transformation (FFT) and conversion in octave bands, in the computer 24, and subsequently the acoustic attenuation provided by the earplug 10 can be estimated from the processed audio signals, i.e. from the sound level measured by each of the microphones 16 and 34.

Subsequently an audio signal is generated by the computer 24 and the sound card 22, which acts upon the automatic switch 20 in such a manner that it changes into the position for the left ear measurement. Then the attenuation measurement described above is performed for the left ear.

Figure 3:
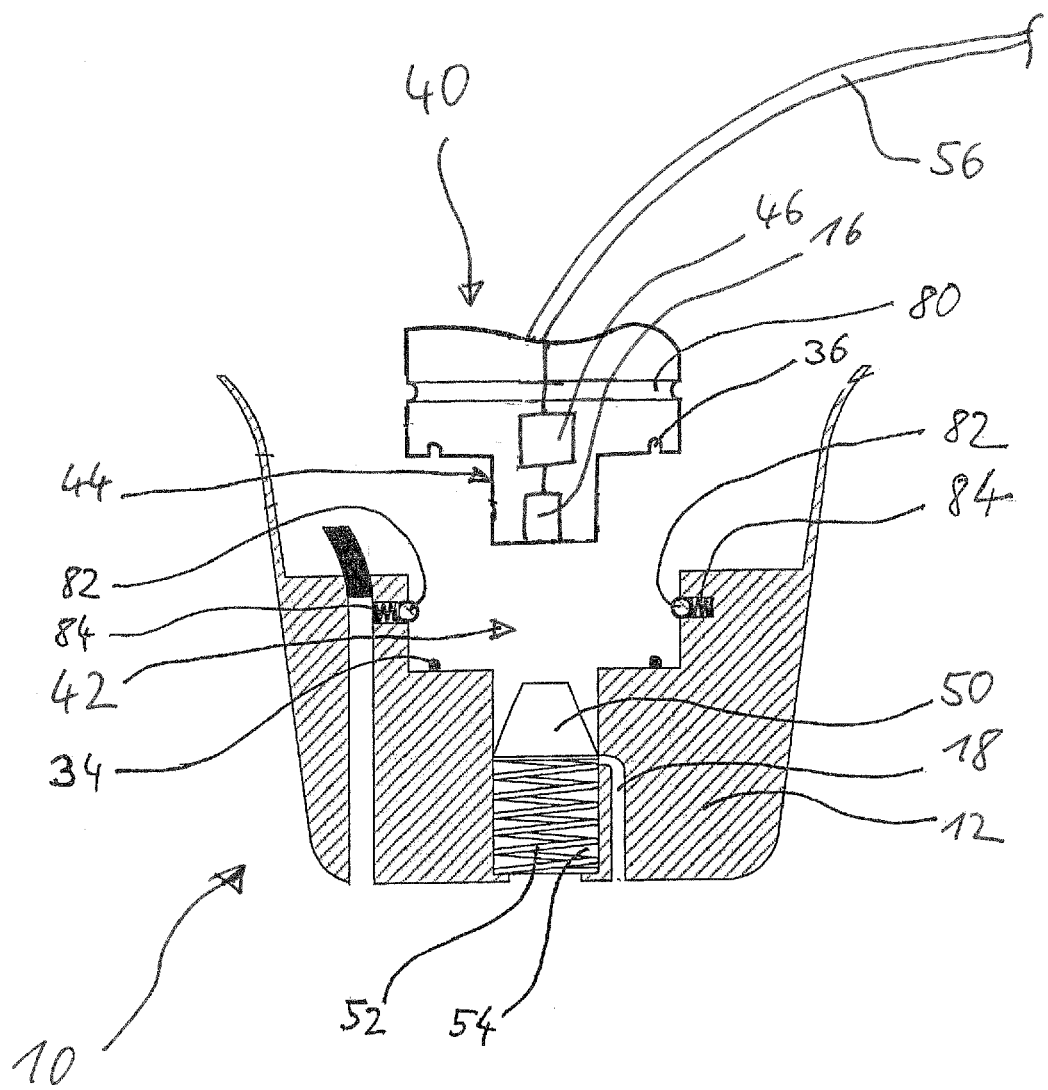
FIG. 3 is a schematic side view, partially in cross-section, of a hearing protection earplug to be used in the invention.

According to a preferred embodiment the earplug 10 is designed such that the microphone 16 is part of a measurement module 40 which can be detachably connected to the shell 12 for carrying out the attenuation measurement. According to FIG. 3 the shell 12 comprises an outer cavity 42 into which the measurement module 40 is to be inserted in a detachable manner. To this end, the shell 12 is provided with radially movable engagement elements 82 which are radially biased towards the centre of the shell 12 by spring elements 84. The engagement elements 82 may be balls. The measurement module 40 is provided with a circumferential groove 80 at the outer surface into which the engagement elements 82 may engage. Further, the cavity 42 is provided with a sealing lip 34 adapted for engagement with a mating groove 36 at the measurement module 40.

In addition, the shell 12 comprises an acoustic valve 48 at the inner end of the cavity 42, which is formed by a conical valve body 50 which is outwardly biased by a spring 52 in a recess 54 and which is tapered outwardly. In the closed position of the valve 48 shown in FIG. 3 the sound passage 18 extending from the cavity 42 to the inner end of the shell 12 is acoustically closed by the valve body 50. However, when the measurement module 40 is inserted into the cavity 42, the valve body 50 is forced inwardly against the biasing force of the spring 52 by an axial extension 44 of the measurement module 40 so that the sound passage 18 is opened for acoustic connection to the microphone 16 of the measurement module.

The measurement module 40 also may comprises an electronic unit 46 connected to the microphone 16 for performing signal processing of the audio signals provided by the microphone 16, for example, pre-amplification. Finally, the measurement module 40 comprises an electrical connection 56 to the automatic switch 20.

When the acoustic attenuation measurement has been terminated, the measurement module 40 may be removed again from the earplug 10 and may be replaced by a functional module (not shown) which is connected to the shell 12 in a detachable manner similar to the measurement module 40. Such functional module may include an acoustic filter and/or a wireless communication unit for the actual use of the earplug 10 by the user.

The mechanism for connecting the measurement module 40 to the earplug 10 in a detachable manner may be any appropriate quickly detachable connection, such as a clipping connection, a screwing connection or a bayonet coupling. Examples of such connections are given in EP 1 674 059 A1.

Figure 4:
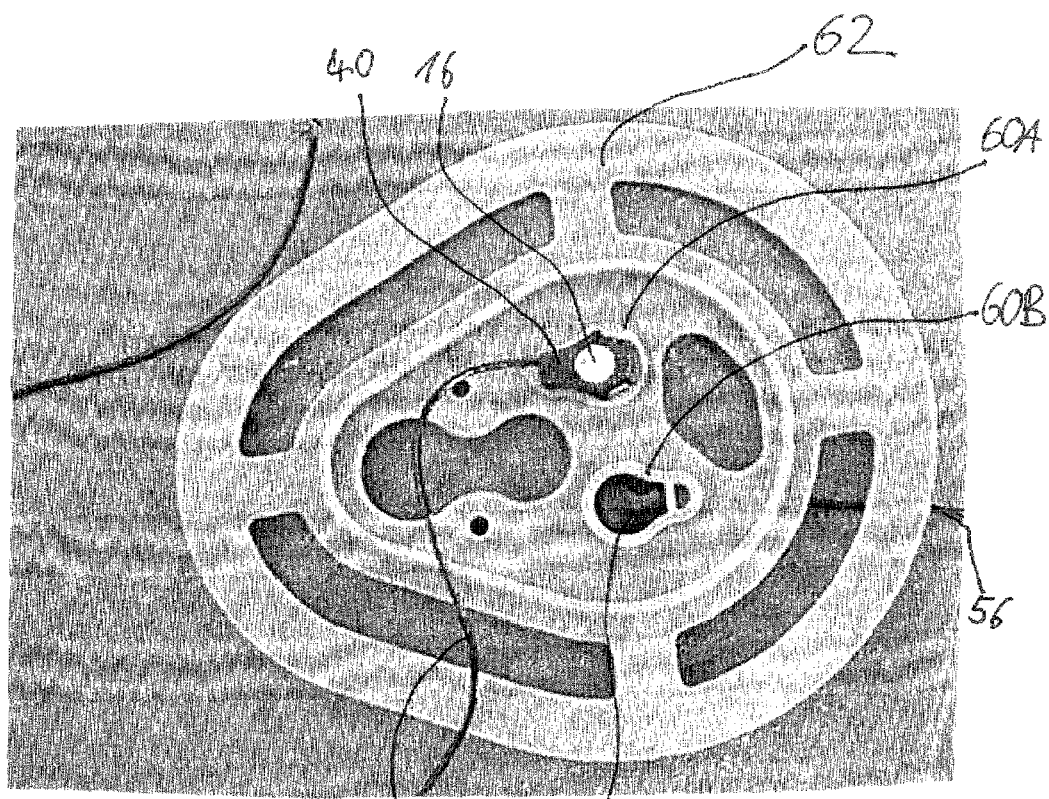
FIG. 4 is a top view of a holder used for calibrating the microphones used in an in-situ acoustic attenuation measurement system according to the invention.
Figure 5:
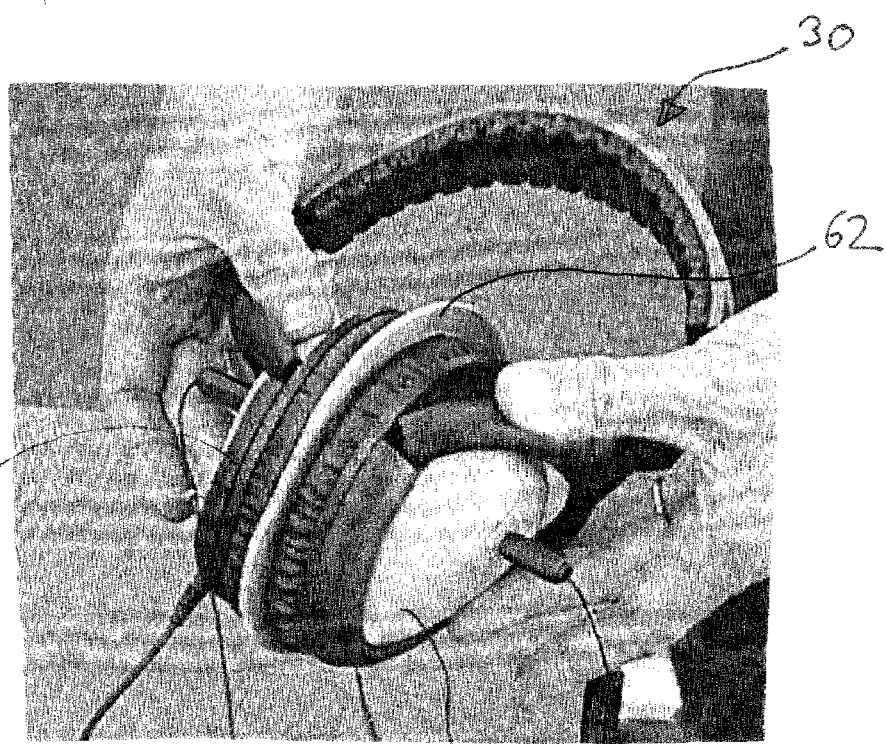
FIG. 5 is a view of a headphone and the holder of FIG. 4 during a calibration measurement according to the invention.

Preferably, the microphone of the hearing protection device and the microphone of the measuring device are calibrated relative to each other prior to the in-situ attenuation measurement. For example, for a measurement device 26 of the type shown in FIG. 1 and an earplug 10 of the type shown FIG. 3 such calibration can be effected by the procedure shown in FIGS. 4 and 5.

In a first step, the measurement modules 40 with the microphone 16 for the left ear earplug 10 and the right ear earplug 10 are mounted in a mating receptacle 60A and 60B, respectively, of a plate-like holder 62, preferably in such a manner that the microphones 16 are facing opposite sides. Each measurement module 40 is connected via the electrical connection 56 in the manner of FIG. 1 via the switch 20 to the sound card 22 and thus to the computer 24, In a second step, the holder 62 with the measurement modules 40 mounted on it is placed between the cups 26 of the measurement headphone 30. The cups 26 are manually pressed together so that the holder 62 is sandwiched in-between in a manner that each cup 26 creates a closed space around the respective measurement module 40, i.e. the respective microphone 16.

Before the actual calibration measurement starts, an audio signal is generated by the computer 24 and the sound card 22 which sets the switch 20, for example, to the right ear position. Then a test audio signal is generated by the computer 24 and the sound card 22 and is supplied to the loudspeaker 32 which creates a corresponding test sound in the closed space 28. This test sound is directly picked-up by the microphone 34 of the right ear cup 26, and a corresponding audio signal is supplied via the sound card 22 to the computer 24. Simultaneously the test sound is also directly picked-up by the microphone 16 of the measurement module 40 mounted in the receptacle 60A, and a corresponding audio signal is supplied via the sound card 22 to the computer 24. The audio signals from the microphones 16 and 34 undergo some signal processing in the computer 24, and subsequently one calibration factor or a set of calibration factors applicable for the microphone 34 of the right ear cup 26 relative to the microphone 16 of the right ear measurement module 40 is determined from the processed audio signals, i.e. from the audio signal level provided by each of the microphones 16 and 34. This calibration factor or set of calibration factors is then used as correction for the audio signal levels obtained in the above described right ear attenuation measurement. In order to be sure that the correct one of the two measurement modules 40 is used in the right ear attenuation measurement, the measurement modules 40 are marked in order to be easily distinguished, for example by a colour code.

Subsequently an audio signal is generated by the computer 24 and the sound card 22, which acts upon the automatic switch 20 in such a manner that it changes into the position for the left ear measurement. Then the calibration measurement described above is performed for the left ear cup 26 and the microphone 16 of the measurement module 40 mounted in the receptacle 60B in order to obtain the calibration factor or set of calibration factors for the microphone 34 of the left ear cup 26 and the microphone 16 of the left ear measurement module 40.

While various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as encompassed by the scope of the appended claims.

What is claimed is:

1. A method for measuring an acoustic attenuation obtained by a hearing protection device worn by a user, comprising:
   positioning said hearing protection device at an ear of said user in an attenuation position, said hearing protection device comprising a microphone oriented towards an ear canal of said user for capturing sound in said user's ear canal;
   positioning a cup-like measuring device at said user's ear in such a manner that a closed space surrounding said hearing protection device positioned in said attenuation position is created by said measuring device, said measuring device comprising a loudspeaker oriented towards said user's ear for providing sound to said closed space and a microphone in said closed space at a distance from said hearing protection device and oriented towards said user's ear for capturing audio signals from sound in said closed space;
   providing a test signal via said loudspeaker, capturing audio signals representative of a level of said test signal in said closed space by said microphone of said measuring device and capturing audio signals representative of a level of said test signal in said user's ear canal by said microphone of said hearing protection device;
   processing said audio signals captured by said microphone of said measuring device and said audio signals captured by said microphone of said hearing protection device and estimating an attenuation provided by said hearing protection device from said processed audio signals.

2. The method of claim 1, wherein processing of said audio signals captured by said microphone of said measuring device and of said audio signals captured by said microphone of said hearing protection device includes Fast Fourier Transformation and conversion in octave bands.

3. The method of claim 1, wherein said hearing protection device and said measuring device are connected via an interface to an external device which generates said test signal and processes said audio signals captured by said microphone of said measuring device and said audio signals captured by said microphone of said hearing protection device and estimates said attenuation provided by said hearing protection device.

4. The method of claim 1, wherein said hearing protection device is an earplug which is inserted at least in part into said user's ear canal.

5. The method of claim 4, wherein said earplug comprises a sound passage extending from said microphone to that end of said earplug facing an ear drum of said user.

6. The method of claim 4, wherein said microphone of said earplug is part of a measurement module which is connected to said earplug in a detachable manner prior to the acoustic attenuation measurement and wherein said measurement module is removed from said earplug after the acoustic attenuation measurement.

7. The method of claim 6, wherein after the acoustic attenuation measurement said measurement module is replaced by a functional module which is connected to said earplug in a detachable manner.

8. The method of claim 7, wherein said functional module includes at least one of an acoustic filter and a wireless communication unit.

9. The method of claim 1, wherein the method is subsequently applied to both ears of said user.

10. The method of claim 1, wherein prior to measuring the acoustic attenuation said microphone of said hearing protection device and said microphone of said measuring device are calibrated relative to each other.

11. The method of claim 10, wherein said microphone of said hearing protection device and said microphone of said measuring device are calibrated relative to each other by:
   mounting said microphone of said hearing protection device at a holder;
   positioning said measuring device at said holder in such a manner that a closed space surrounding said microphone of said hearing protection device mounted at said holder is created by said measuring device;
   providing a test signal via said loudspeaker, capturing audio signals representative of a level of said test signal in said closed space by said microphone of said measuring device and capturing audio signals representative of said level of said test signal in said closed space by said microphone of said hearing protection device; and
   comparing said audio signals captured by said microphone of said hearing protection device and said audio signals captured by said microphone of said measuring device.

12. The method of claim 11, wherein said microphone of said hearing protection device is mounted at said holder separate from said hearing protection device for the calibration measurement and is detachably mounted at said hearing protection device after the calibration measurement has been terminated.

13. The method of claim 12, wherein said holder has a plate-like shape and wherein said measuring device is a cup of a headphone, which is pressed against said holder for creating said enclosed space.

14. The method of claim 13, wherein said holder is placed between said two cups of said headphone which are pressed together.

15. System for measuring an acoustic attenuation obtained by a hearing protection device worn by a user, comprising:
   a hearing protection device capable of being positioned at an ear of said user in an attenuation position and comprising a microphone oriented towards an ear canal of said user for capturing audio signals from sound in said user's ear canal;

a cup-like measuring device capable of being positioned at said user's ear in such a manner that a closed space surrounding said hearing protection device positioned in said attenuation position is created by said measuring device, said measuring device comprising a loudspeaker oriented towards said user's ear for providing sound to said closed space and a microphone in said closed space so as to be located at a distance from said hearing protection device and oriented towards said user's ear for capturing audio signals from sound in said closed space when the measuring device is positioned at said user's ear;

means for providing a test signal via said loudspeaker to said closed space; and means for processing said audio signals captured by said microphone of said measuring device and said audio signals captured by said microphone of said hearing protection device and estimating an attenuation provided by said hearing protection device from said processed audio signals.

16. The system of claim 15, wherein said hearing protection device and said measuring device comprise an interface for being connected to an external device adapted for generating said test signal and for processing said audio signals captured by said microphone of said measuring device and said audio signals captured by said microphone of said hearing protection device and estimating said attenuation provided by said hearing protection device.

17. The system of claim 15, wherein said hearing protection device is an earplug comprising a shell to be inserted into said user's ear canal.

18. The system of claim 17, wherein the shell comprises a sound passage extending from said microphone to that end of said earplug which is to face said user's ear drum.

19. The system of claim 17, wherein said microphone of said earplug is part of a measurement module which is detachably connected to said shell.

20. The system of claim 19, wherein said shell comprises valve means which are moveable, upon connecting said measurement module to said shell, from a closed position in which said valve means acoustically closes said sound passage into an open position in which said valve means acoustically opens said sound passage, said valve means being biased towards said closed position in order to acoustically close said sound passage when said measurement module is removed from said shell, and wherein said microphone is acoustically connected to said sound passage when said measurement module is connected to said shell.

21. The system of claim 15, wherein said measuring device is a cup of a headphone.

* * * * *